United States Patent
Burris et al.

(10) Patent No.: US 6,599,899 B2
(45) Date of Patent: Jul. 29, 2003

(54) BENZOXAZINONES AS PEROXISOME PROLIFERATOR ACTIVATED RECEPTOR GAMMA MODULATORS AND METHOD OF TREATMENT

(75) Inventors: Thomas P. Burris, Noblesville, IN (US); Philip J. Rybczynski, Branchburg, NJ (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 18 days.

(21) Appl. No.: 09/853,798

(22) Filed: May 11, 2001

(65) Prior Publication Data

US 2002/0103193 A1 Aug. 1, 2002

Related U.S. Application Data

(60) Provisional application No. 60/203,859, filed on May 12, 2000.

(51) Int. Cl.$^7$ .................. A61K 31/536; A61K 31/5365
(52) U.S. Cl. ..................................... 514/230.5; 544/105
(58) Field of Search ......................... 544/105; 514/230.5

(56) References Cited

U.S. PATENT DOCUMENTS 5,854,242 A * 12/1998 Frechette et al.

FOREIGN PATENT DOCUMENTS

| WO | WO 9604260 | 2/1996 |
|---|---|---|
| WO | WO 9717333 | 5/1997 |
| WO | WO 9728167 | 8/1997 |
| WO | WO 9920614 | 4/1999 |
| WO | WO 9119702 | 12/1999 |

OTHER PUBLICATIONS

PCT Search Report of PCT/US01/15320, Mailed Dec. 27, 2001.

Hilliard, James J., et al.: "Multiple mechanisms of action for inhibitors of histidine protein kinases from bacterial two–component systems" Antimicrob. Agents Chemother. (1999) 43(7), 1693–1699.

* cited by examiner

*Primary Examiner*—Richard L. Raymond

(57) ABSTRACT

The invention is directed to benzoxazinone derivatives useful as peroxisome proliferator activated receptor gamma (PPARγ) modulators. Pharmaceutical compositions comprising compounds of the present invention and methods of treating conditions such as NIDDM and obesity are also disclosed.

17 Claims, No Drawings

BENZOXAZINONES AS PEROXISOME PROLIFERATOR ACTIVATED RECEPTOR GAMMA MODULATORS AND METHOD OF TREATMENT

CROSS REFERENCE TO RELATED APPLICATIONS

This application claims priority from U.S. Serial No. 60/203,859, filed May 12, 2000.

FIELD OF THE INVENTION

This invention relates to benzoxazinone derivatives useful for the treatment of Non-Insulin Dependant Diabetes Mellitus (NIDDM) and complications thereof and disorders related to lipid metabolism and energy homeostasis such as obesity. The compound acts through the Peroxisome Proliferator Activated Receptor gamma (PPARγ), and is orally active as PPARγ modulator.

BACKGROUND OF THE INVENTION

Diabetes is a disease caused by multiple factors and characterized by hyperglycemia which may be associated with increased and premature mortality due to an increased risk for microvascular and macrovascular diseases such as nephropathy, neuropathy, retinopathy, atherosclerosis, polycystic ovary syndrome (PCOS), hypertension, ischemia, stroke, and heart disease. Type I diabetes (IDDM) results from genetic deficiency of insulin, the hormone regulating glucose metabolism. Type II diabetes is known as non-insulin dependent diabetes mellitus (NIDDM), and is due to a profound resistance to insulin regulatory effect on glucose and lipid metabolism in the main insulin-sensitive tissues, i.e., muscle, liver and adipose tissue. This insulin resistance or reduced insulin sensitivity results in insufficient insulin activation of glucose uptake, oxidation and storage in muscle and inadequate insulin repression of lipolysis in adipose tissue as well as glucose production and secretion in liver. Many Type II diabetics are also obese, and obesity is believed to cause and/or exacerbate many health and social problems such as coronary heart disease, stroke, obstructive sleep apnoea, gout, hyperlipidemia, osteoarthritis, reduced fertility, and impaired psychosocial function.

A class of compounds, thiazolidinediones (glitazones), have been suggested to be capable of ameliorating many symptoms of NIDDM by binding to the peroxisome proliferator activated receptor (PPAR) family of receptors. They increase insulin sensitivity in muscle, liver and adipose tissue in several animal models of NIDDM resulting in correction of the elevated plasma levels of glucose, triglycerides and nonesterified free fatty acids without any occurrence of hypoglycemia. However, undesirable effects have occurred in animal and/or human studies including cardiac hypertrophy, hemadilution and liver toxicity.

Most PPARγ agonists currently in development have thiazolidinedione ring as their common chemical structure. PPARγ agonists have been demonstrated to be extremely useful for the treatment of NIDDM and other disorders involving insulin resistance. Recently, troglitazone, rosiglitazone, and pioglitazone have been approved for treatment of type II diabetes. There is also indication that benzimidazole-containing thiazolidinedione derivatives may be used to treat irritable bowel disorder (IBD), inflammation, and cataract (JP 10195057).

JP 09012576 (Yoshitake et al.) discloses benzothiazine derivatives stated as useful therapeutic agents for circulatory system disease and glaucoma.

JP 09012575 (Hiroaki et al.) discloses benzoxazine and benzothiazine derivatives stated to be useful as prophylactic drugs and/or therapeutic drugs in hyperlipemia, hyperglycemia, obesity, diseases attributable to sugar tolerance insufficiency, hypertension, osteoporosis, cachexia, and complications of diabetes such as retinopathy, nephrosis, neuropathy, cataract, coronary artery disease and arteriosclerosis.

WO 99/20614 (Lohray et al.) discloses β-aryl-α-oxysubstituted alkylcarboxylic acids stated as antiobesity and hypocholesterolemic compounds which may have agonist activity against PPARα and/or PPARγ, and optionally inhibit HMG CoA reductase.

WO 97/17333 (Frechette et al.) and U.S. Pat. Nos. 5,696,117 and 5,854,242 to Frechette et al. generically disclose compounds of Formula I. They describe benzoxazine and pyrido-oxazine compounds having a moiety of a fused phenyl or fused pyridyl, pharmaceutical compositions containing the compounds, and methods for their production and their use in treating bacterial infections.

U.S. Pat. No. 5,859,051 to Adams et al. discloses the following acetylphenols,

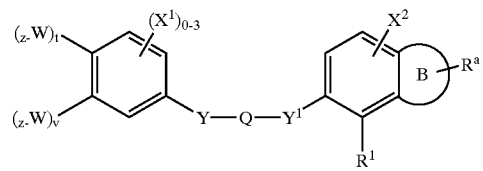

wherein substituents are as described in the reference, which are stated to be useful as antiobesity and antidiabetic compounds without the thiazolidinedione moiety.

WO 99/38845 (De La Brouse-Elwood et al.) discloses the following compounds,

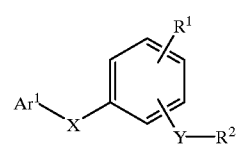

wherein substituents are as described in the reference, which are stated to modulate the PPARγ receptor and are stated as useful in the diagnosis and treatment of type II diabetes (and complications thereof) and inflammatory disorders.

SUMMARY OF THE INVENTION

The present invention is directed to the compounds of Formulae I,

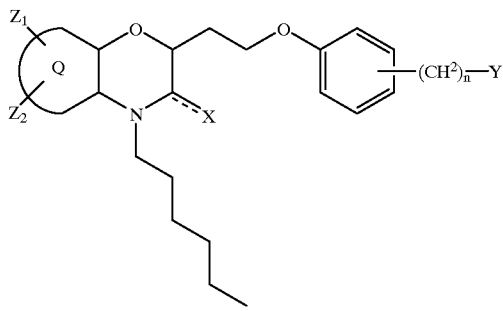

or an optical isomer, enantiomer, diastereomer, racemate or racemic mixture thereof, ester, prodrug form, or a pharmaceutically acceptable salt thereof, wherein Q is a fused phenyl or fused pyridyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or halogen;

X is hydrogen or oxygen;

n is an integer from 0–3; and

Y is selected from
(a) $NHR_1R_2$, $N^+R_1R_2R_3$;
(b) $NHC(NR_4)NR_5$;
(c) $CO_2H$, CHO;
(d) $CH(R_6)COOH$, $CH(R_6)COOCH_3$, $CH=CHR_7$, $CH=C(COOH)_2$;
(e) a moiety of the formula

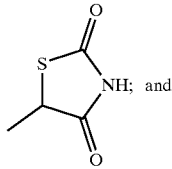

(f) 5-tetrazolyl, wherein $R_1$, $R_2$ and $R_3$ are independently hydrogen, $C_1$–$C_6$ alkyl, or t-butoxycarbonyl;

$R_4$ and $R_5$ are independently t-butoxycarbonyl or hydrogen, or $R_4$ and $R_5$ may be joined together to form an imidazoline, imidazolyl or pyrimidine ring;

$R_6$ is hydrogen, hydroxy, or halogen; and $R_7$ is $CO_2H$ or $C(O)NH(CH_2)_pOH$ wherein p is an integer from 1–4.

In particular, the present invention is directed to the following compounds:

benzeneacetic acid, 2-[2-(4-hexyl-3,4-dihydro-3-oxo-2H-1,4-benzoxazin-2-yl)ethoxy]-;

benzeneacetic acid, 2-[2-[(2R)-4-hexyl-3,4-dihydro-3-oxo-2H-1,4-benzoxazin-2-yl]ethoxy]-; and benzeneacetic acid, 2-[2-[(2S)-4-hexyl-3,4-dihydro-3-oxo-2H-1,4-benzoxazin-2-yl]ethoxy]-.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An embodiment of the invention is a method of treating a subject suffering from a disorder in glucose and lipid metabolism including, but not limited to, NIDDM, obesity, nephropathy, neuropathy, retinopathy, atherosclerosis polycystic ovary syndrome, ischemia, hypertension, stroke, and heart disease, which comprises administering to the subject a therapeutically effective amount of any of the compounds or pharmaceutical compositions described above.

Another example of the invention is a method of inhibiting in a subject the onset of a disorder in glucose and lipid metabolism, which comprises administering to the subject a prophylactically effective dose of any compound of the compounds or pharmaceutical compositions described above.

DETAILED DESCRIPTION OF THE INVENTION

The present invention provides a compound of Formula I,

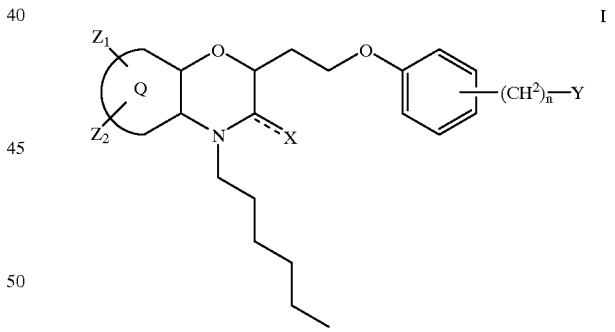

or an optical isomer, enantiomer, diastereomer, racemate or racemic mixture thereof, ester, prodrug form, or a pharmaceutically acceptable salt thereof, wherein Q is a fused phenyl or fused pyridyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or halogen;

X is hydrogen or oxygen;

n is an integer from 0–3; and

Y is selected from
(a) $NHR_1R_2$, $N^+R_1R_2R_3$;
(b) $NHC(NR_4)NR_5$;
(c) $CO_2H$, CHO;
(d) $CH(R_6)COOH$, $CH(R_6)COOCH_3$, $CH=CHR_7$, $CH=C(COOH)_2$;
(e) a moiety of the formula

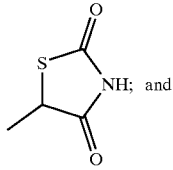

(f) 5-tetrazolyl, wherein $R_1$, $R_2$ and $R_3$ are independently hydrogen, $C_1$–$C_6$ alkyl, or t-butoxycarbonyl;

$R_4$ and $R_5$ are independently t-butoxycarbonyl or hydrogen, or $R_4$ and $R_5$ may be joined together to form an imidazoline, imidazolyl or pyrimidine ring;

$R_6$ is hydrogen, hydroxy, or halogen; and $R_7$ is $CO_2H$ or $C(O)NH(CH_2)_pOH$ wherein p is an integer from 1–4.

Preferably, the present invention provides benzoxazinone compounds selected from benzeneacetic acid, 2-[2-(4-hexyl-3,4-dihydro-3-oxo-2H-1,4-benzoxazin-2-yl)ethoxy]-;

benzeneacetic acid, 2-[2-[(2R)-4-hexyl-3,4-dihydro-3-oxo-2H-1,4-benzoxazin-2-yl]ethoxy]-; and benzeneacetic acid, 2-[2-[(2S)-4-hexyl-3,4-dihydro-3-oxo-2H-1,4-benzoxazin-2-yl]ethoxy]-;

which are represented by Formulae Ia, Ib, and Ic, respectively:

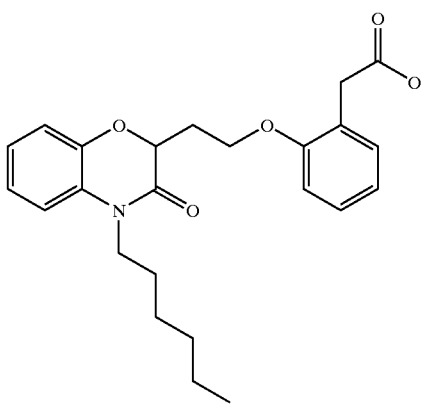

Ia

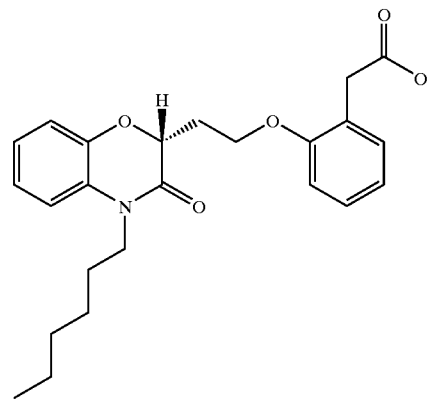

Ib

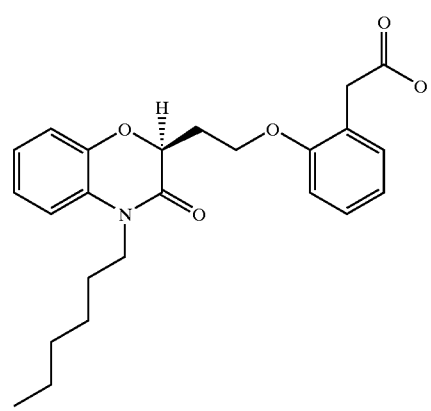

Ic

Unless otherwise noted, "alkyl" and "alkoxy" as used herein, whether used alone or as part of a substituent group, include straight and branched chains having 1 to 10 carbon atoms, or any number within this range. For example, alkyl radicals include methyl, ethyl, n-propyl, isopropyl, n-butyl, isobutyl, sec-butyl, t-butyl, n-pentyl, 3-(2-methyl)butyl, 2-pentyl, 2-methylbutyl, neopentyl, n-hexyl, 2-hexyl, 2-methylpentyl, and the like. Alkoxy radicals are oxygen ethers formed from the previously described straight or branched chain alkyl groups. Cycloalkyl groups contain 3 to 8 ring carbons and preferably 5 to 7 ring carbons. Similarly, alkenyl and alkynyl groups include straight and branched chain alkenes and alkynes having 1 to 10 carbon atoms, or any number within this range.

Unless otherwise stated, "aryl," employed alone or in combination with other terms (e.g., aryloxy, arylthioxy, arylalkyl), is an aromatic radical which can be a single ring or multiple rings which are fused together or linked covalently. Illustrative aryl groups may be phenyl or naphthyl optionally substituted with one or more of the following: H, $C_1$–$C_{10}$ alkyl, $C_3$–$C_8$ cycloalkyl, $COOR^1$, $CONR^1R^2$, OH, $C_1$–$C_{10}$ alkyl ether, aryl or heterocyclyl ether, $OC(O)R^1$, $OC(O)OR^1$, $OC(O)NR^1R^2$, $NR^1R^2$, $NR^3C(O)R^1$, $NR^3C(O)OR^1$, $NR^3C(O)NR^1R^2$, halogen or halo (F, Cl, Br, I).

"Heterocyclyl" or "heterocycle" is a 3- to 8-member saturated or unsaturated heterocyclic group containing 1–4 nitrogens, an oxygen, or a sulfur atom; or one nitrogen and either oxygen or sulfur.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein.

As used herein, the term "composition" is intended to encompass a product comprising the specified ingredients in the specified amounts, as well as any product which results, directly or indirectly, from combinations of the specified ingredients in the specified amounts.

The term "subject" as used herein, refers to an animal, preferably a mammal, most preferably a human, who has been the object of treatment, observation or experiment.

Methods are known in the art for determining therapeutically and prophylactically effective doses for the instant pharmaceutical composition. The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. The term "prophylactically effective amount" refers to that amount of active compound or pharmaceutical agent that inhibits in a subject the onset of a disorder as being sought by a researcher, veterinarian, medical doctor or other clinician, the delaying of which disorder is mediated by modulating the actions of PPARγ.

Depending upon the biological environment (e.g., cell type, pathological condition of the host, etc.), these compounds can activate or block the actions of PPARγ. The utility of the compounds to treat the above disorders in glucose and lipid metabolism can be determined according to the procedures described herein. The present invention therefore provides a method of treating disorders in glucose and lipid metabolism in a subject in need thereof which comprises administering any of the compounds as defined herein in a quantity effective to treat such disorders. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier. The pharmaceutical composition may contain between about 0.1 mg and 1000 mg, preferably about 100 to 500 mg, of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

To prepare the pharmaceutical compositions of this invention, one or more compounds of the present invention or salt thereof of the invention as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 30 mg/kg of body weight per day. Preferably, the range is from about 0.03 to about 15 mg/kg of body weight per day, most preferably, from about 0.05 to about 10 mg/kg of body weight per day. The compounds may be administered on a regimen of 1 to 2 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action.

For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the products may be varied over a wide range from 1 to 1000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 30 mg/kg of body weight per day. Particularly, the range is from about 0.03 to about 15 mg/kg of body weight per day, and more particularly, from about 0.05 to about 10 mg/kg of body weight per day. The compounds may be administered on a regimen of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compound of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

From Formula I it is evident that some of the compounds of the invention may have one or more asymmetric carbon atoms in their structure. As represented in Formulae Ib and Ic, the exo/endo orientation of a single bond is indicated by dotted hash (into the page) and solid hash (out of the page), respectively. It is intended that the present invention includes within its scope the stereochemically pure isomeric forms of the compounds as well as their racemates. Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, Third Edition, John Wiley & Sons, 1999. The protecting groups may be removed at a convenient subsequent stage using methods known from the art.

The chemistry of preparing compounds of Formula I is described in detail in U.S. Pat. Nos. 5,696,117 and 5,854,242, both to Frechette et al., and WO 97/17333 (Frechette et al.), all of which are hereby incorporated by reference in their entirety.

This invention will be better understood by reference to the schemes and examples that follow, but those skilled in the art will readily appreciate that these are only illustrative of the invention as described more fully in the claims which follow thereafter.

The compounds of Formula I may be synthesized with the chemistry outlined in Scheme 1 wherein $Z_1$ is hydrogen, halogen, $C_1$–$C_6$ alkyl, $C_1$–$C_6$ alkoxy, phenyl, OH, amino, nitro, sulfonylamino or trifluoromethyl;

$Z_2$ is hydrogen or halogen;

A is hexyl;

n is an integer from 0–3; and

G is selected from
(a) $NHR_1R_2$, $N^+R_1R_2R_3$;
(b) $NHC(NR_4)NR_5$;
(c) $CO_2H$, CHO;
(d) $CH(R_6)COOH$, $CH(R_6)COOCH_3$, $CH=CHR_7$, $CH=C(COOH)_2$;
(e) a moiety of the formula

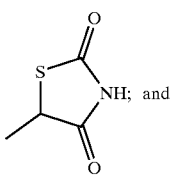

(f) 5-tetrazolyl,
wherein
$R_1$, $R_2$ and $R_3$ are independently hydrogen, $C_1$–$C_6$ alkyl, or t-butoxycarbonyl;
$R_4$ and $R_5$ are independently t-butoxycarbonyl or hydrogen, or $R_4$ and $R_5$ may be joined together to form an imidazoline, imidazolyl or pyrimidine ring;
$R_6$ is hydrogen, hydroxy, or halogen; and
$R_7$ is $CO_2H$ or $C(O)NH(CH_2)_pOH$ wherein p is an integer from 1–4.

Scheme 1

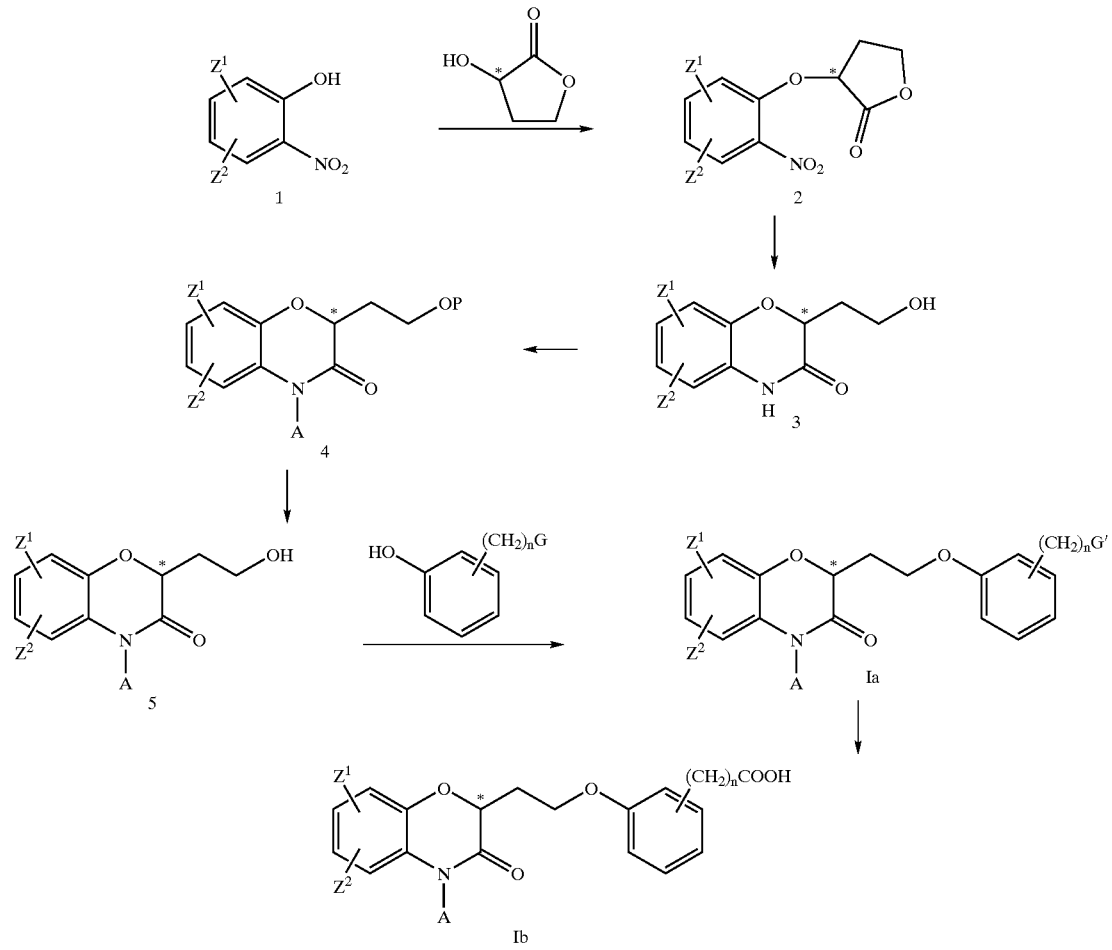

In accordance with Scheme 1, the benzoxazinones can be made by conversion of a compound of the Formula 1 to a compound of the Formula 2. For example, when a chiral alcohol, such as (S)- or (R)-2-hydroxybutyrolactone, is coupled under conditions that preserve stereochemical integrity, either by retention or inversion of absolute configuration, a chiral compound of the Formula 2 isobtained. A particularly useful example of this transformation is the use of the Mitsunobu reaction, which is delineated in the examples. In this reaction, a compound of the Formula 1 is exposed to a chiral secondary alcohol, such as 2-hydroxybutyrolactone, a phosphine, such as triphenylphosphine or tributylphosphine, and an azo compound, such as diethylazo dicarboxylate or the like, in a variety of non-protic solvents, such as THF, benzene, or DMF, to provide the corresponding ether of the general Formula 2. Maintaining stereochemical integrity throughout the course of the process provides chiral products Ia and Ib. For example, the ether of the general Formula 2 is reduced to yield compound of the Formula 3 with a reagent such as hydrogen gas or ammonium formate, and a catalyst, such as palladium or platinum, in an appropriate solvent, such as methanol, ethanol, or ethyl acetate, at an appropriate temperature. The primary alcohol is protected with a variety of reagents, such as tert-butyldimethylsilyl chloride and imidazole, in a non-protic polar solvent, such as DMF or THF, with or without heating. The choice of protecting group may be easily determined by one skilled in the art. Substitution of the amide of the general Formula 3 by deprotonation with a base, such as an alkali metal hydride, in a non-protic polar solvent, such as DMF (N,N-dimethylformamide) or THF (tetrahydrofuran), and addition of an alkyl halide or mesylate or tosylate or the like followed by deprotection of the alcohol gives compounds of general Formula 4. The choice of deprotection methods may be easily determined by one skilled in the art. The ether of the general Formula 5 can be obtained by a reaction such as the Mitsunobu reaction as described by Frechette, et al., and delineated in the following examples. Deprotection of the alcohol gives the corresponding compounds of Formula 6 that can be further converted to the alkyl aryl ether of Formula Ia by adding HO—Ar—$(CH_2)_n$G' (G' is G as described above other than —COOH), which are commercially available and/or may be readily prepared by known methods. Thus deprotection of the ester to the acid yields the desired product of Formula Ib.

The following examples are intended to illustrate the invention but not to limit it.

EXAMPLE 1

Benzeneacetic acid, 2-[2-(4-hexyl-3,4-dihydro-3-oxo-2H-1,4-benzoxazin-2-yl)ethoxy]-

Proton NMR was performed on a Bruker 300 MHz NMR spectrometer; J values are reported in Hertz.

A mixture of 2-nitrophenol (20 g, 0.14 mol) and $K_2CO_3$ (25.2 g, 0.18 mol) in 280 mL DMF (N,N-dimethylformamide) was cooled to 0° C. 2-Bromobutyrolactone was added dropwise, the reaction was stirred for 45 min at 0° C., then stirred at room temperature for 3 hours (h). The mixture was poured into 2 L water containing approx. 200 g salt, and the solution was washed with 6×100 mL of 1:1 diethyl ether/ethyl acetate. The combined organics were washed with 2×100 mL sat'd aq. $K_2CO_3$, 5×100 mL water and 100 mL brine, dried ($Na_2SO_4$), and filtered. Solvent was removed in vacuo to yield a phenolic ether (2(3H)-furanone, dihydro-3-(2-nitrophenoxy)-) as an off-white solid (21.88 g, 0.1 mol). $^1$H (CDCl$_3$): 7.84 (d, 1H, J=7.9), 7.57 (t, 1H, J=7.5), 7.49 (d, 1H, J=7.9), 7.16 (t, 1H, J=7.5), 5.03 (t, 1H, J=7.4), 4.58 (m, 1H), 4.42 (m, 1H), 2.8–2.6 (m, 2H).

The phenolic ether (2(3H)-furanone, dihydro-3-(2-nitrophenoxy)-, 21.88 g, 0.1 mol) was suspended in 200 mL ethanol and 200 mL EtOAc, then shaken overnight with 10% Pd/C and $H_2$ (45 psi) at room temperature. The solution was filtered through Celite and solvent was removed in vacuo. The crude benzoxazinone (2H-1,4-benzoxazin-3(4H)-one, 2-(2-hydroxyethyl)-) was dissolved in 200 anh. DMF, imidazole (14.1 g, 0.21 mol) was added, and the solution was cooled to 0° C. tert-Butyldimethylsilyl chloride (31.2 g, 0.21 mol) was added as a solid and the reaction was stirred overnight, under $N_2$, as the bath thawed. The reaction was poured into 1.4 L water containing approx. 200 g salt, and washed with 4×150 mL of 4:1 diethyl ether/EtOAc. The combined organics were washed with 6×100 mL water and 100 mL brine. The organics were dried ($Na_2SO_4$), filtered, and solvent was removed in vacuo. The product was isolated by silica gel chromatography with hexane/ethyl acetate. Obtain the silyl ether (2H-1,4-benzoxazin-3(4H)-one, 2-[2-[[(1,1-dimethylethyl)dimethylsilyl]oxy]ethyl]-) as a volatile solid (7.0 g, 0.022 mol). $^1$H (CDCl$_3$): 6.89 (m, 3H), 6.80 (m, 1H), 4.70 (m, 1H), 3.78 (m, 2H), 2.15 (m, 1H), 1.94 (m, 1H), 0.83 (s, 9H), 0.07 (s, 6H).

A solution of (2H-1,4-benzoxazin-3(4H)-one, 2-[2-[[(1,1-dimethylethyl)dimethylsilyl]oxy]ethyl]-, 15.00 g, 0.049 mol) in 250 mL anh. DMF, under $N_2$, was cooled to 0° C. Sodium hydride (75% dispersion in oil, 1.62 g, 0.054 mol) was added in two portions of 0.81 g with five minute intervals between additions. The solution was stirred for and additional 40 min at 0° C. 1-Iodohexane (7.2 mL, 0.049 mol) in 20 mL DMF was added dropwise, the ice bath was replaced with an oil bath, and the solution was stirred at 65° C. for 5 h. The mixture was cooled to room temperature and poured into 1.5 L water containing approx. 200 g salt. The aqueous mixture was washed with 4×125 mL of 1:1 diethyl ether/ethyl acetate. The combined organic were washed with 6×125 mL water and 125 mL brine. The organics were dried ($Na_2SO_4$), filtered, and solvent was removed in vacuo. The product was isolated by silica gel chromatography with hexane/ethyl acetate. The alkylated amide (2H-1,4-benzoxazin-3(4H)-one, 2-[2-[[(1,1-dimethylethyl)dimethylsilyl]oxy]ethyl]-4-hexyl-) was obtained as a colorless oil (18.03 g, 0.046 mol). $^1$H (CDCl$_3$): 7.0 (m, 4H), 4.72 (dd, 1H, J=10.0, 3.6), 3.95–3.75 (m, 4H), 2.17 (m, 1H), 1.93 (m, 1H), 1.33 (m, 6H), 0.89 (s, 12H), 0.07 (s, 6H).

Silyl ether (2H-1,4-benzoxazin-3(4H)-one, 2-[2-[[(1,1-dimethylethyl)dimethylsilyl]oxy]ethyl]-4-hexyl-) was dissolved in 75 mL methanol and 3 mL water. Methanesulfonic acid (0.5 mL) was added and the mixture was stirred at room temperature for 2 h. Solvent was removed in vacuo and the product was isolated by silica gel chromatography with hexane/ethyl acetate. The primary alcohol (2H-1,4-benzoxazin-3(4H)-one, 4-hexyl-2-(2-hydroxyethyl)-) was obtained as a colorless oil (11.16 g, 0.04 mol). $^1$H (CDCl$_3$) 7.01 (m, 4H), 4.69 (t, 1H, J=7.0), 3.88 (m, 4H), 2.44 (t, 1H, J=5.8), 2.20 (m, 2H), 1.65 (m, 2H), 1.33 (m, 6H), 0.89 (br t, 3H).

A solution of (2H-1,4-benzoxazin-3(4H)-one, 4-hexyl-2-(2-hydroxyethyl)-, 11.16 g, 0.04 mol), (2-hydroxyphenyl)acetic acid (10 g, 0.06 mol), and tributylphosphine (14.9 mL, 0.06 mol) in 670 mL anhydrous benzene, under $N_2$, was cooled to 4° C. 1,1'-(Azodicarbonyl)dipiperidine (15.1 g, 0.06 mol) was added in one portion, and the solution was stirred, with an overhead stirrer, at room temperature overnight. The organic phase was washed with 4×50 mL 2 N NaOH, 50 mL water and 50 mL brine. The organics were dried ($Na_2SO_4$), filtered, and solvent was removed in vacuo. The product was purified by silica gel chromatography with hexane/ethyl acetate. The ester (benzeneacetic acid, 2-[2-(4-hexyl-3,4-dihydro-3-oxo-2H-1,4-benzoxazin-2-yl)ethoxy]-, methyl ester) was obtained as a colorless oil (9.7 g, 0.023 mol). $^1$H (CDCl$_3$): 7.28–6.89 (m, 8H), 4.76 (dd, 1H, J=9.4, 4), 4.28–4.21 (m, 2H), 3.92 (t, 2H, J=7.7), 3.60 (two singlets, 5H), 2.49 (m, 1H), 2.23 (m, 1H), 1.66 (m, 2H), 1.34 (m, 6H), 0.89 (br t, 3H).

A solution of (benzeneacetic acid, 2-[2-(4-hexyl-3,4-dihydro-3-oxo-2H-1,4-benzoxazin-2-yl)ethoxy]-, methyl ester, 26.5 g, 0.062 mol) in 500 mL THF was cooled to 0°

C. 200 mL 0.95 N aq. LiOH (0.19 mol LiOH) at 10° C. was added in one portion. The solution was stirred at room temperature overnight, open to air. The solution was poured into 1.2 L water and 11 mL conc. HCl. Extract with 4×120 mL dichloromethane. The combined organics were washed with 120 mL water/60 mL brine combination, dried ($MgSO_4$), and filtered. Solvent was removed in vacuo. The oily residue was diluted with 1 L pentane and 200 mL diethyl ether, heated on a steam bath, and scratched with a frosted glass rod until the material became a white solid. The mixture was cooled to 0° C. for 1.5 hours, then filtered and washed with 2×100 mL pentane. The amorphous white solid (the title compound) was dried in a vacuum oven at 40° C. (21.5 g, 0.052 mol). m.p. 80.0–81.5° C. $^1$H ($CDCl_3$) 7.28–6.89 (m, 8H), 4.88 (dd, 1H, J=9, 3.5), 4.20 (m, 2H), 3.91 (t, 2H, J=7.8), 3.67 (d, 1H, J=16), 3.60 (d, 1H, J=16), 2.43 (m, 1H), 2.23 (m, 1H), 1.65 (m, 2H), 1.33 (m, 6H), 0.88 (br t, 3H).

EXAMPLE 2

Benzeneacetic acid, 2-[2-[(2R)-4-hexyl-3,4-dihydro-3-oxo-2H-1,4-benzoxazin-2-yl]ethoxy]-

The steps below describe the stereospecific synthesis of benzeneacetic acid, 2-[2-[(2R)-4-hexyl-3,4-dihydro-3-oxo-2H-1,4-benzoxazin-2-yl]ethoxy]-.

(S)-(−)-α-Hydroxy-γ-butyrolactone was purchased and used in the first step. Proton NMR was performed on a Bruker 300 MHz NMR spectrometer, J values are reported in Hertz. Stereochemical integrity was confirmed for 2(3H)-furanone, dihydro-3-(2-nitrophenoxy)-, (3R)-, 2H-1,4-benzoxazin-3(4H)-one, 4-hexyl-2-(2-hydroxyethyl)-, (2R)-, and final product (the title compound) with chiral HPLC. The analytical chiral HPLC was performed on a Hewlett-Packard 1090 Series II AminoQuant HPLC fitted with a Daicel Chemical Industries, LTD Chiralpak AD column (4.6 mm×25 cm). Sample concentration was 1 mg/mL in eluting solvent, flow rate was 1 mL/min, UV detection was at 254 nm. Solvent and retention time of the chiral and racemic are listed with the individual experimental.

2(3H)-furanone, dihydro-3-(2-nitrophenoxy)-, (3R)-

A solution of 2-nitrophenol (27.8 g, 0.2 mol), (S)-(−)-α-hydroxy-γ-butyrolactone (15.3 mL, 0.2 mol) and triphenylphosphine (78.6 g, 0.3 mol) in 550 mL anhydrous THF, under $N_2$, was cooled to −20° C. A room temperature solution of diethylazodicarboxylate (DEAD, 47.5 mL, 0.3 mol) in 20 mL THF was added dropwise over 30 min. The reaction was stirred for 17 h as the cold bath thawed. The mixture was poured into 3 L water containing approx. 200 g salt, and the solution was washed with 6×100 mL of 1:1 diethyl ether/ethyl acetate. The combined organics were washed with 5×100 mL water and 100 mL brine, dried ($Na_2SO_4$), and filtered. The crude product was chromatographed on silica using $CH_2Cl_2$, then 95:5 $CH_2Cl_2$/ethyl acetate to yield slightly impure product and impure product. A second column was run on the impure product from the first column, eluting with 7:3 $CH_2Cl_2$/hexane, then $CH_2Cl_2$. The product from the second column was crystallized from ethyl acetate/hexane to yield 12.28 g of 2(3H)-furanone, dihydro-3-(2-nitrophenoxy)-, (3R)- as a pale yellow solid. The supernatant was combined with the slightly impure 2(3H)-furanone, dihydro-3-(2-nitrophenoxy)-, (3R)- from the first column and crystallized from ethyl acetate/hexane to yield 8.88 g of 2(3H)-furanone, dihydro-3-(2-nitrophenoxy)-, (3R)- as a pale yellow solid (12.28 g+8.88 g=21.16 g, 0.095 mol). $^1$H ($CDCl_3$): 7.84 (d, 1H, J=7.9), 7.57 (t, 1H, J=7.5), 7.49 (d, 1H, J=7.9), 7.16 (t, 1H, J=7.5), 5.03 (t, 1H, J=7.4), 4.58 (m, 1H), 4.42 (m, 1H), 2.8–2.6 (m, 2H). By HPLC the enantiomeric purity was >99% for each crystalline sample (8:2 hexane/isopropanol, ret. time chiral=13.8 min, ret. time racemic=11.1 min, 13.7 min).

2H-1,4-benzoxazin-3(4H)-one, 2-[2-[[(1,1-dimethylethyl)dimethylsilyl]oxy]ethyl]-, (2R)-

The phenolic ether (2(3H)-furanone, dihydro-3-(2-nitrophenoxy)-, (3R)-, 21.16 g, 0.095 mol) was suspended in 400 mL ethanol, then shaken for 3 h with 10% Pd/C and $H_2$ (45 psi) at room temperature. The solution was filtered through Celite and solvent was removed in vacuo. The crude benzoxazinone (2H-1,4-benzoxazin-3(4H)-one, 2-(2-hydroxyethyl)-, (2R)-, calc. for 18.4 g, 0.095 mol) was dissolved in 200 anh. DMF, imidazole (16.3 g, 0.24 mol) was added, and the solution was cooled to 0° C. tert-Butyldimethylsilyl chloride (28.6 g, 0.19 mol) was added as a solid and the reaction was stirred overnight, under $N_2$, as the bath thawed. The reaction was poured into 1.4 L water containing approx. 200 g salt, and washed with 4×150 mL of 4:1 diethyl ether/dichloromethane. The combined organics were washed with 6×100 mL water and 100 mL brine. The organics were dried ($Na_2SO_4$), filtered, and solvent was removed in vacuo. The product was isolated by silica gel chromatography with hexane/ethyl acetate. Obtain the silyl ether (2H-1,4-benzoxazin-3(4H)-one, 2-[2-[[(1,1-dimethylethyl)dimethylsilyl]oxy]ethyl]-, (2R)-) as a volatile solid (26.75 g, 0.087 mol). $^1$H ($CDCl_3$): 6.89 (m, 3H), 6.80 (m, 1H), 4.70 (m, 1H), 3.78 (m, 2H), 2.15 (m, 1H), 1.94 (m, 1H), 0.83 (s, 9H), 0.07 (s, 6H). HPLC was not obtained due to the lipophilicity of the compound.

2H-1,4-benzoxazin-3(4H)-one, 2-[2-[[(1,1-dimethylethyl)dimethylsilyl]oxy]ethyl]-4-hexyl-, (2R)-

A solution of (2H-1,4-benzoxazin-3(4H)-one, 2-[2-[[(1,1-dimethylethyl)dimethylsilyl]oxy]ethyl]-, (2R)-, 26.75 g, 0.087 mol) in 435 mL anh. DMF, under $N_2$, was cooled to 0° C. Sodium hydride (75% dispersion in oil, 2.48 g, 0.083 mol) was added in four portions of 0.62 g with five minute intervals between additions. The solution was stirred for and additional 40 min at 0° C. 1-Iodohexane (12.8 mL, 0.087 mol) in 25 mL DMF was added dropwise, the ice bath was replaced with an oil bath, and the solution was stirred at 65° C. overnight. The mixture was cooled to room temperature and poured into 3 L water containing approx. 200 g salt. The aqueous mixture was washed with 4×125 mL of 1:1 diethyl ether/ethyl acetate. The combined organic were washed with 6×125 mL water and 125 mL brine. The organics were dried ($Na_2SO_4$), filtered, and solvent was removed in vacuo. The product was isolated by silica gel chromatography with hexane/ethyl acetate. The alkylated amide (2H-1,4-benzoxazin-3(4H)-one, 2-[2-[[(1,1-dimethylethyl)dimethylsilyl]oxy]ethyl]-4-hexyl-, (2R)-) was obtained as a colorless oil. $^1$H ($CDCl_3$): 7.0 (m, 4H), 4.72 (dd, 1H, J=10.0, 3.6), 3.95–3.75 (m, 4H), 2.17 (m, 1H), 1.93 (m, 1H), 1.33 (m, 6H), 0.89 (s, 12H), 0.07 (s, 6H).

2H-1,4-benzoxazin-3(4H)-one, 4-hexyl-2-(2-hydroxyethyl)-, (2R)-

Silyl ether (2H-1,4-benzoxazin-3(4H)-one, 2-[2-[[(1,1-dimethylethyl)dimethylsilyl]oxy]ethyl]-4-hexyl-, (2R)-) was dissolved in 150 mL methanol. 6 N aq. HCl (0.5 mL) was added and the mixture was stirred at room temperature for 5 h. Solvent was removed in vacuo and the product was isolated by silica gel chromatography with hexane/ethyl acetate. The primary alcohol (2H-1,4-benzoxazin-3(4H)-one, 4-hexyl-2-(2-hydroxyethyl)-, (2R)-) was obtained as a colorless oil (16.7 g, 0.060 mol). $^1$H ($CDCl_3$): 7.01 (m, 4H), 4.69 (t, 1H, J=7.0), 3.88 (m, 4H), 2.44 (t, 1H, J=5.8), 2.20 (m, 2H), 1.65 (m, 2H), 1.33 (m, 6H), 0.89 (br t, 3H). By HPLC the enantiomeric purity was 97.4:2.1 (9:1 hexane/isopropanol, ret. time chiral=7.5 min, ret. time racemic=7.6 min, 8.5 min).

Benzeneacetic acid, 2-[2-[(2R)-4-hexyl-3,4-dihydro-3-oxo-2H-1,4-benzoxazin-2-yl]ethoxy]-, methyl ester A solution of (2H-1,4-benzoxazin-3(4H)-one, 4-hexyl-2-(2-hydroxyethyl)-, (2R)-) (16.7 g, 0.06 mol), (2-hydroxyphenyl)acetic acid (15 g, 0.09 mol), and tributylphosphine (22.4 mL, 0.09 mol) in 1 L anhydrous benzene, under $N_2$, was cooled to 10° C. 1,1'-(Azodicarbonyl)dipiperidine (22.7 g, 0.09 mol) was added in one portion, and the solution was stirred, with an overhead stirrer, at room temperature overnight. 130 mL water was added and stirring continued for 40 minutes. The mixture was transferred to a separatory funnel. The organic phase was washed with 4×100 mL water, and 100 mL brine. The organics were dried ($Na_2SO_4$), filtered, and solvent was removed in vacuo. The product was purified by silica gel chromatography with hexane/ethyl acetate. The ester (benzeneacetic acid, 2-[2-[(2R)-4-hexyl-3,4-dihydro-3-oxo-2H-1,4-benzoxazin-2-yl]ethoxy]-, methyl ester) was obtained as a colorless oil (24.3 g, 0.057 mol). $^1H$ ($CDCl_3$): 7.28–6.89 (m, 8H), 4.76 (dd, 1H, J=9.4, 4), 4.28–4.21 (m, 2H), 3.92 (t, 2H, J=7.7), 3.60 (two singlets, 5H), 2.49 (m, 1H), 2.23 (m, 1H), 1.66 (m, 2H), 1.34 (m, 6H), 0.89 (br t, 3H).

Benzeneacetic acid, 2-[2-[(2R)-4-hexyl-3,4-dihydro-3-oxo-2H-1,4-benzoxazin-2-yl]ethoxy]-

A solution of (benzeneacetic acid, 2-[2-[(2R)-4-hexyl-3,4-dihydro-3-oxo-2H-1,4-benzoxazin-2-yl]ethoxy]-, methyl ester) (24.3 g, 0.057 mol) in 500 mL THF was cooled to 0° C. 200 mL 0.85 N aq. LiOH (0.17 mol LiOH) at 10° C. was added in one portion. The solution was stirred at room temperature overnight, open to air. The solution was poured into 1 L water and the solution was brought to pH 4 by portionwise addition of 28.5 mL of 6 N HCl. Extract with 4×120 mL dichloromethane. The combined organics were washed with 120 mL water/60 mL brine combination, dried ($MgSO_4$), and filtered. Solvent was removed in vacuo. The oily residue was diluted with 1 L pentane and 200 mL diethyl ether, heated on a steam bath, and scratched with a frosted glass rod until the material became a white solid. The mixture was cooled to 0° C. for 1.5 hours, then filtered and washed with 2×100 mL pentane. The amorphous white solid (the title compound) was dried in a vacuum oven at 40° C. (17.5 g, 0.043 mol). m.p. 80.0–81.5° C. $[\alpha]^D_{25}$=+31.2° (c=1, $CHCl_3$). $^1H$ ($CDCl_3$) 7.28–6.89 (m, 8H), 4.88 (dd, 1H, J=9, 3.5), 4.20 (m, 2H), 3.91 (t, 2H, J=7.8), 3.67 (d, 1H, J=16), 3.60 (d, 1H, J=16), 2.43 (m, 1H), 2.23 (m, 1H), 1.65 (m, 2H), 1.33 (m, 6H), 0.88 (br t, 3H). Passed elemental analysis (C, H, N). By HPLC the enantiomeric purity was 99:1 (80:20:0.1 hexane/isopropanol/trifluoroacetic acid, ret. time chiral=7.2 min, ret. time racemic=7.2 min, 8.7 min).

aP2 Assay for Antagonist

Twenty-four hours after the initial seeding of the 96-well plates by hand (around 20,000/well), the differentiation assay may be initiated. Medium may be removed and replaced with 150 ul of differentiation medium containing vehicle (DMSO) or test compounds with a known aP2 activator or such aP2 activator alone. Cells may be returned to incubator for 24 hours culture. At the termination of the challenge, medium may be removed and 100 µl of lysis buffer may be added to initiate the bDNA aP2 mRNA assay. The branched DNA assay may be performed according to the manufacturer's protocol (Bayer Diagnostics; Emeryville, Calif.). Result may be expressed as percent inhibition of aP2 mRNA production activated by the aP2 activator. $IC_{50}$'s may be determined by non-linear regression with a sigmoidal fit curve.

Following the challenge of the preadipocytes, cells may be lysed with lysis buffer (Bayer Diagnostics) containing the aP2 oligonucleotides. After a 15 minutes incubation at 53° C. or 30 minutes at 37° C. incubator, 70 µl of the lysis buffer from each well may be added to a corresponding capture well (preincubated with 70 µl of blocking buffer (Bayer Diagnostics)). The capture plate may be incubated overnight at 53° C. in a plate incubator (Bayer Diagnostics). After this incubation, the bDNA and labeled probes may be annealed as directed by the manufacturer. Following a 30-minute incubation with the luminescent alkaline phosphatase substrate, dioxitane, the luminescence may be quantitated in a Dynex MLX microtiter plate luminometer. Oligonucleotide probes designed to anneal to the aP2 mRNA and function in the bDNA mRNA detection system are designed with ProbeDesigner software (Bayer Diagnostics). This software package analyzes a target sequence of interest with a series of algorithms in order to determine which regions of the sequence can perform as locations for capture, label, or spacer probe annealing. The sequence of the oligonucleotides are as follows:

| Sequence | ID |
|---|---|
| CATTTTGTGAGTTTTCTAGGATTATTCTTTTCTCTTGGAAAGAAAGT | SEQ ID NO.1 |
| ATGTTAGGTTTGGCCATGCCTTTCTCTTGGAAAGAAAGT | SEQ ID NO.2 |
| CCTCTCGTTTTCTCTTTATGGTTTTCTCTTGGAAAGAAAGT | SEQ ID NO.3 |
| GCTTATGCTCTCTCATAAACTCTCGTGGTTTCTCTTGGAAAGAAAGT | SEQ ID NO.4 |
| CCAGGTACCTACAAAAGCATCACATTTAGGCATAGGACCCGTGTCT | SEQ ID NO.5 |
| GCCCACTCCTACTTCTTTCATATAATCATTTAGGCATAGGACCCGTGTCT | SEQ ID NO.6 |
| AGCCACTTTCCTGGTGGCAAATTTAGGCATAGGACCCGTGTCT | SEQ ID NO.7 |
| CATCCCCATTCACACTGATGATCTTTAGGCATAGGACCCGTGTCT | SEQ ID NO.8 |
| GTACCAGGACACCCCCATCTAAGGTTTTTAGGCATAGGACCCGTGTCT | SEQ ID NO.9 |
| GGTTGATTTTCCATCCCATTTCTGCACATTTTAGGCATAGGACCCGTGTCT | SEQ ID NO.10 |
| GCATTCCACCACCAGTTTATCATTTTAGGCATAGGACCCGTGTCT | SEQ ID NO.11 |
| GCGAACTTCAGTCCAGGTCAACGTCCCTTGTTTAGGCATAGGACCCGTGTCT | SEQ ID NO.12 |

-continued

| | |
|---|---|
| TCCCACAGAATGTTGTAGAGTTCAATTTTAGGCATAGGACCCGTGTCT | SEQ ID NO.13 |
| AAAACAACAATATCTTTTTGAACAATATATTTAGGCATAGGACCCGTGTCT | SEQ ID NO.14 |
| TCAAAGTTTTCACTGGAGACAAGTTT | SEQ ID NO.15 |
| AAAGGTACTTTCAGATTTAATGGTGATCA | SEQ ID NO.16 |
| CTGGCCCAGTATGAAGGAAATCTCAGTATTTTT | SEQ ID NO.17 |
| TCTGCAGTGACTTCGTCAAATTC | SEQ ID NO.18 |
| ATGGTGCTCTTGACTTTCCTGTCA | SEQ ID NO.19 |
| AAGTGACGCCTTTCATGAC | SEQ ID NO.20 | aP2 Assay for Agonist

The procedure is described in detail in Burris et al., *Molecular Endocrinology*, 1999, 13:410, which is hereby incorporated by reference, and aP2 assay results of agonist intrinsic activity may be presented as fold increase over vehicle in induction of aP2 mRNA production. Table 1 below sets forth the mass spectra data and the agonist intrinsic activity of some compounds of the present invention.

TABLE 1

Some compounds of this invention

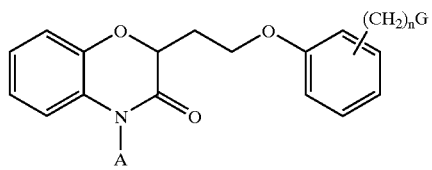

| Compound No. | A | Pos(n)G | MS; MH+ | Agonist Intrinsic Activity |
|---|---|---|---|---|
| 1 | n-Hex | 2(1)COOH | 412 | 40.4 |
| 2 | R enant.; n-Hex | 2(1)COOH | 412 | — |

TABLE 1-continued

Some compounds of this invention

| Compound No. | A | Pos(n)G | MS; MH+ | Agonist Intrinsic Activity |
|---|---|---|---|---|
| 3 | S enant.; n-Hex | 2(1)COOH | 412 | — |
| 4 | n-Hex | 2(1)COOCH₃ | 426 | — |

Keys: Hex = hexyl.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A method of treating a subject suffering from a disorder in glucose and lipid metabolism, which comprises administering to the subject a therapeutically effective amount of the compound of the Formula (I),

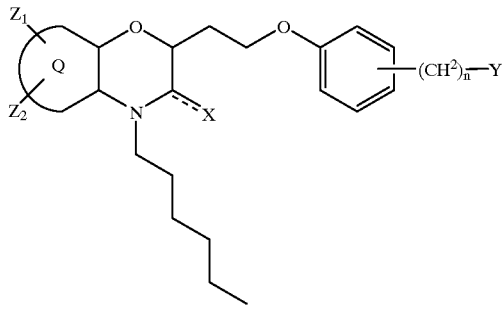

or an optical isomer, enantiomer, diastereomer, racemate or racemic mixture thereof, ester, prodrug form, or a pharmaceutically acceptable salt thereof, wherein Q is a fused phenyl or fused pyridyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or halogen;

X is hydrogen or oxygen;

n is an integer from 0–3; and

Y is selected from
(a) $N^+HR_1R_2$, $N^+R_1R_2R_3$;
(b) $NHC(=NR_4)NHR_5$;
(c) $CO_2H$, CHO;
(d) $CH(R_6)COOH$, $CH(R_6)COOCH_3$, $CH=CHR_7$, $CH=C(COOH)_2$;
(e) a moiety of the formula

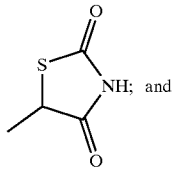

(f) 5-tetrazolyl, wherein $R_1$, $R_2$ and $R_3$ are independently hydrogen, $C_1$–$C_6$ alkyl, or t-butoxycarbonyl;

$R_4$ and $R_5$ are independently t-butoxycarbonyl or hydrogen, or $R_4$ and $R_5$ may be joined together to form an imidazoline, imidazolyl or pyrimidine ring;

$R_6$ is hydrogen, hydroxy, or halogen; and $R_7$ is $CO_2H$ or $C(O)NH(CH_2)_pOH$ wherein p is an integer from 1–4.

2. A method of inhibiting in a subject the onset of a disorder in glucose and lipid metabolism, which comprises administering to the subject a prophylactically effective dose of a compound of the Formula (I),

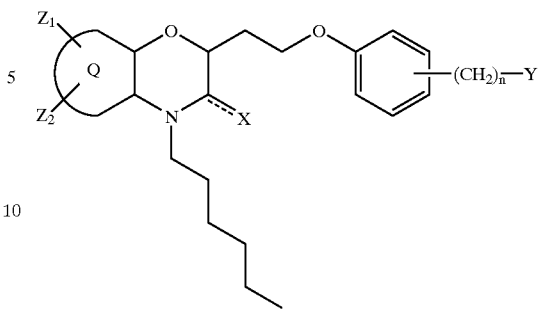

or an optical isomer, enantiomer, diastereomer, racemate or racemic mixture thereof, ester, prodrug form, or a pharmaceutically acceptable salt thereof, wherein Q is a fused phenyl or fused pyridyl moiety;

$Z_1$ is hydrogen, halogen, $C_1$–$C_6$ alkyl, $C_1$–$C_6$ alkoxy, phenyl, hydroxy, amino, nitro, sulfonylamino or trifluoromethyl;

$Z_2$ is hydrogen or halogen;

X is hydrogen or oxygen;

n is an integer from 0–3; and

Y is selected from
(a) $N^+HR_1R_2$, $N^+R_1R_2R_3$;
(b) $NHC(=NR_4)NHR_5$;
(c) $CO_2H$, CHO;
(d) $CH(R_6)COOH$, $CH(R_6)COOCH_3$, $CH=CHR_7$, $CH=C(COOH)_2$;
(e) a moiety of the formula

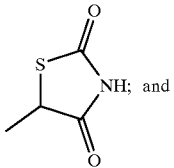

(f) 5-tetrazolyl, wherein $R_1$, $R_2$ and $R_3$ are independently hydrogen, $C_1$–$C_6$ alkyl, or t-butoxycarbonyl;

$R_4$ and $R_5$ are independently t-butoxycarbonyl or hydrogen, or $R_4$ and $R_5$ may be joined together to form an imidazoline, imidazolyl or pyrimidine ring;

$R_6$ is hydrogen, hydroxy, or halogen; and $R_7$ is $CO_2H$ or $C(O)NH(CH_2)_pOH$ wherein p is an integer from 1–4.

3. A method of claim 1 wherein said disorder is a condition of reduced insulin sensitivity.

4. A method of claim 3 wherein said condition of reduced insulin sensitivity is Non-Insulin Dependant Diabetes Mellitus or obesity.

5. A method of claim 1 wherein said disorder is selected from nephropathy, neuropathy, retinopathy, atherosclerosis polycystic ovary syndrome, ischemia, hypertension, stroke, and heart disease.

6. A method of claim 1, wherein Y is COOH or COOCH$_3$.

7. A method of claim 2, wherein Y is COOH or COOCH$_3$.

8. A method of claim 1, wherein $R_6$ is hydrogen or halogen when n is 1.

9. A method of claim 6, wherein the compound is selected from benzeneacetic acid, 2-[2-(4-hexyl-3,4-dihydro-3-oxo-2H-1,4-benzoxazin-2-yl)ethoxy]-;

benzeneacetic acid, 2-[2-[(2R)-4-hexyl-3,4-dihydro-3-oxo-2H-1,4-benzoxazin-2-yl]ethoxy]-; and benzeneacetic acid, 2-[2-[(2S)-4-hexyl-3,4-dihydro-3-oxo-2H-1,4-benzoxazin-2-yl]ethoxy]-.

10. A method of claim 9, wherein said compound is benzeneacetic acid, 2-[2-(4-hexyl-3,4-dihydro-3-oxo-2H-1,4-benzoxazin-2-yl)ethoxy]-.

11. A method of claim 9, wherein said compound is benzeneacetic acid, 2-[2-[(2R)-4-hexyl-3,4-dihydro-3-oxo-2H-1,4-benzoxazin-2-yl]ethoxy]-.

12. A method of claim 9, wherein said compound is benzeneacetic acid, 2-[2-[(2S)-4-hexyl-3,4-dihydro-3-oxo-2H-1,4-benzoxazin-2-yl]ethoxy]-.

13. A method of claim 2, wherein $R_6$ is hydrogen or halogen when n is 1.

14. A method of claim 7, wherein the compound is selected from benzeneacetic acid, 2-[2-(4-hexyl-3,4-dihydro-3-oxo-2H-1,4-benzoxazin-2-yl)ethoxy]-;

benzeneacetic acid, 2-[2-[(2R)-4-hexyl-3,4-dihydro-3-oxo-2H-1,4-benzoxazin-2-yl]ethoxy]-; and benzeneacetic acid, 2-[2-[(2S)-4-hexyl-3,4-dihydro-3-oxo-2H-1,4-benzoxazin-2-yl]ethoxy]-.

15. A method of claim 14, wherein said compound is benzeneacetic acid, 2-[2-(4-hexyl-3,4-dihydro-3-oxo-2H-1,4-benzoxazin-2-yl)ethoxy]-.

16. A method of claim 14, wherein said compound is benzeneacetic acid, 2-[2-[(2R)-4-hexyl-3,4-dihydro-3-oxo-2H-1,4-benzoxazin-2-yl]ethoxy]-.

17. A method of claim 14, wherein said compound is benzeneacetic acid, 2-[2-[(2S)-4-hexyl-3,4-dihydro-3-oxo-2H-1,4-benzoxazin-2-yl]ethoxy]-.

* * * * *

SEQUENCE LISTING

<160> NUMBER OF SEQ ID NOS: 20

<210> SEQ ID NO 1
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 1
cattttgtga gttttctagg attattcttt tctcttggaa agaaagt          47

<210> SEQ ID NO 2
<211> LENGTH: 39

```
<212> TYPE: DNA
<213> ORGANISM: Artificial Sequence
<220> FEATURE:
<223> OTHER INFORMATION: Description of Artificial Sequence: primer

<400> SEQUENCE: 2
atgttaggtt tggccatgcc tttctcttgg aaagaaagt                              39

<210> SEQ ID NO 3
<211> LENGTH: 41
<212> TYPE: DNA
<213> ORGANISM: Artificial Sequence
<220> FEATURE:
<223> OTHER INFORMATION: Description of Artificial Sequence: primer

<400> SEQUENCE: 3
cctctcgttt tctctttatg gttttctctt ggaaagaaag t                           41

<210> SEQ ID NO 4
<211> LENGTH: 47
<212> TYPE: DNA
<213> ORGANISM: Artificial Sequence
<220> FEATURE:
<223> OTHER INFORMATION: Description of Artificial Sequence: primer

<400> SEQUENCE: 4
gcttatgctc tctcataaac tctcgtggtt tctcttggaa agaaagt                     47

<210> SEQ ID NO 5
<211> LENGTH: 46
<212> TYPE: DNA
<213> ORGANISM: Artificial Sequence
<220> FEATURE:
<223> OTHER INFORMATION: Description of Artificial Sequence: primer

<400> SEQUENCE: 5
ccaggtacct acaaaagcat cacatttagg cataggaccc gtgtct                      46

<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: primer

<400> SEQUENCE: 6
gcccactcct acttctttca tataatcatt taggcatagg acccgtgtct                  50

<210> SEQ ID NO 7
<211> LENGTH: 43
<212> TYPE: DNA
<213> ORGANISM: Artificial Sequence
<220> FEATURE:
<223> OTHER INFORMATION: Description of Artificial Sequence: primer

<400> SEQUENCE: 7
agccactttc ctggtggcaa atttaggcat aggacccgtg tct                         43

<210> SEQ ID NO 8
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 8
```

```
catccccatt cacactgatg atctttaggc ataggacccg tgtct                45

<210> SEQ ID NO 9
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 9
gtaccaggac accccatct aaggttttta ggcataggac ccgtgtct              48

<210> SEQ ID NO 10
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 10
ggttgatttt ccatcccatt tctgcacatt ttaggcatag gacccgtgtc t         51

<210> SEQ ID NO 11
<211> LENGTH: 45
<212> TYPE: DNA
<213> ORGANISM: Artificial Sequence
<220> FEATURE:
<223> OTHER INFORMATION: Description of Artificial Sequence: primer

<400> SEQUENCE: 11
gcattccacc accagtttat cattttaggc ataggacccg tgtct                45

<210> SEQ ID NO 12
<211> LENGTH: 52
<212> TYPE: DNA
<213> ORGANISM: Artificial Sequence
<220> FEATURE:
<223> OTHER INFORMATION: Description of Artificial Sequence: primer

<400> SEQUENCE: 12
gcgaacttca gtccaggtca acgtcccttg tttaggcata ggacccgtgt ct        52

<210> SEQ ID NO 13
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 13
tcccacagaa tgttgtagag ttcaatttta ggcataggac ccgtgtct             48

<210> SEQ ID NO 14
<211> LENGTH: 51
<212> TYPE: DNA
<213> ORGANISM: Artificial Sequence
<220> FEATURE:
<223> OTHER INFORMATION: Description of Artificial Sequence: primer

<400> SEQUENCE: 14
aaaacaacaa tatcttttg aacaatatat ttaggcatag gacccgtgtc t          51

<210> SEQ ID NO 15
<211> LENGTH: 26
<212> TYPE: DNA
<213> ORGANISM: Artificial Sequence
```

```
<220> FEATURE:
<223> OTHER INFORMATION: Description of Artificial Sequence: primer

<400> SEQUENCE: 15
tcaaagtttt cactggagac aagttt                                          26

<210> SEQ ID NO 16
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 16
aaaggtactt tcagatttaa tggtgatca                                       29

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: primer

<400> SEQUENCE: 17
ctggcccagt atgaaggaaa tctcagtatt ttt                                  33

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 18
tctgcagtga cttcgtcaaa ttc                                             23

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 19
atggtgctct tgactttcct gtca                                            24

<210> SEQ ID NO 20
<211> LENGTH: 19
<212> TYPE: DNA
<213> ORGANISM: Artificial Sequence
<220> FEATURE:
<223> OTHER INFORMATION: Description of Artificial Sequence: primer

<400> SEQUENCE: 20
aagtgacgcc tttcatgac                                                  19
```